(12) United States Patent
Lee et al.

(10) Patent No.: US 9,232,775 B2
(45) Date of Patent: Jan. 12, 2016

(54) **GENETICALLY ENGINEERED MOUSE MODEL FOR AUTISM SPECTRUM DISORDER HAVING DELETION OF *SHANK2* GENE AND USE THEREOF**

(71) Applicants: Industry-Academic Cooperation Foundation, Yonsei University, Seoul (KR); Seoul National University R&DB Foundation, Seoul (KR); Korea Advanced Institute of Science and Technology, Daejeon (KR)

(72) Inventors: Min Goo Lee, Gyeonggi-do (KR); Bong Kiun Kaang, Seoul (KR); Eunjoon Kim, Daejeon (KR)

(73) Assignees: Industry-Academic Cooperation Foundation, Yonsei University, Seoul (KR); Seoul National University R&DB Foundation, Seoul (KR); Korea Advanced Institute of Science and Technology, Daejeon (KR)

( * ) Notice: Subject to any disclaimer, the term of this patent is extended or adjusted under 35 U.S.C. 154(b) by 26 days.

(21) Appl. No.: 13/958,040

(22) Filed: Aug. 2, 2013

(65) Prior Publication Data

US 2014/0041062 A1   Feb. 6, 2014

Related U.S. Application Data

(60) Provisional application No. 61/679,186, filed on Aug. 3, 2012, provisional application No. 61/681,110, filed on Aug. 8, 2012.

(51) Int. Cl.
| | | |
|---|---|---|
| *A01K 67/027* | (2006.01) | |
| *A01K 67/00* | (2006.01) | |
| *G01N 33/50* | (2006.01) | |
| *C07K 14/705* | (2006.01) | |
| *C12N 15/85* | (2006.01) | |

(52) U.S. Cl.
CPC ............ *A01K 67/0276* (2013.01); *C07K 14/705* (2013.01); *C12N 15/8509* (2013.01); *G01N 33/5008* (2013.01); *G01N 33/5082* (2013.01); *A01K 67/0275* (2013.01); *A01K 2217/054* (2013.01); *A01K 2217/056* (2013.01); *A01K 2227/105* (2013.01); *A01K 2267/0306* (2013.01); *A01K 2267/0318* (2013.01); *C12N 2015/8536* (2013.01)

(58) Field of Classification Search
CPC ........... A01K 67/0275; A01K 67/0276; A01K 2217/054; A01K 2217/056; A01K 2227/105; A01K 2267/0318
USPC ......................................... 800/9, 18
See application file for complete search history.

(56) References Cited

PUBLICATIONS

Goldman et al., 2004, Med Sci Monit, vol. 10, No. 11, RA274-285.*
Sigmund, C., Jun. 2000, Arterioscler. Thromb. Vasc. Biol., p. 1425-1429.*
Houdebine, Louis-Marie, 2007, Methods in Molecular Biology, vol. 360, p. 163-202.*
Carstea et al., 2009, World Journals of Stem Cells, vol. 1, No. 1, p. 22-29.*
Jiang et al., 2013, Neuron, vol. 78, p. 8-27.*
Won et al., Jun. 2012, Nature, vol. 486, p. 261-265.*

* cited by examiner

*Primary Examiner* — Shin Lin Chen
(74) *Attorney, Agent, or Firm* — Mintz Levin Cohn Ferris Glovsky and Popeo, P.C.; Kongsik Kim; Richard B. Emmons

(57) ABSTRACT

The present disclosure relates to an ASD genetically engineered model carrying a deletion of Shank2 gene and having reduced NMDA receptor function. According to the present disclosure, genetically engineered mice that show the clinical features of ASD due to the deletion of the Shank2 gene can be obtained, and the genetically engineered mice can be effectively used to screen candidate therapeutic agents.

1 Claim, 25 Drawing Sheets

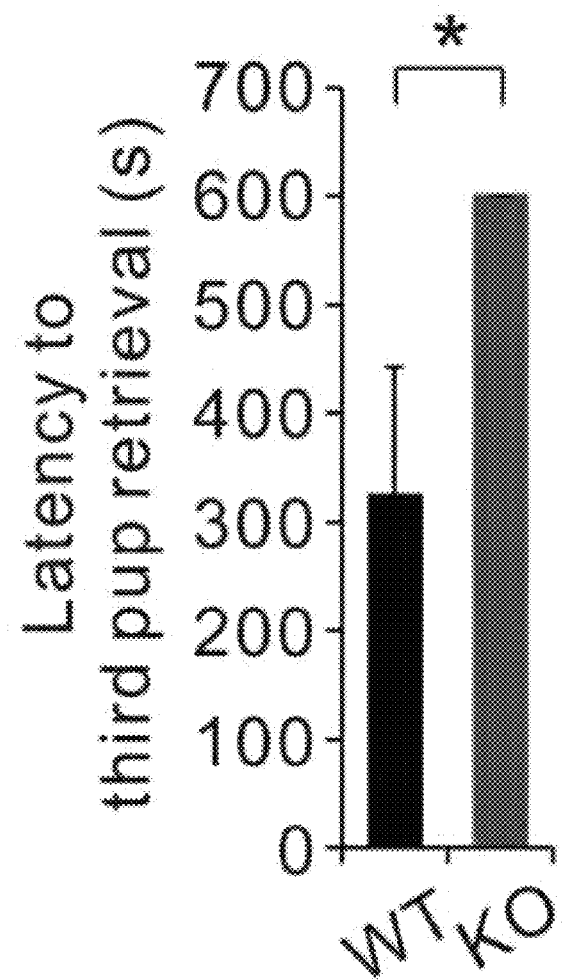

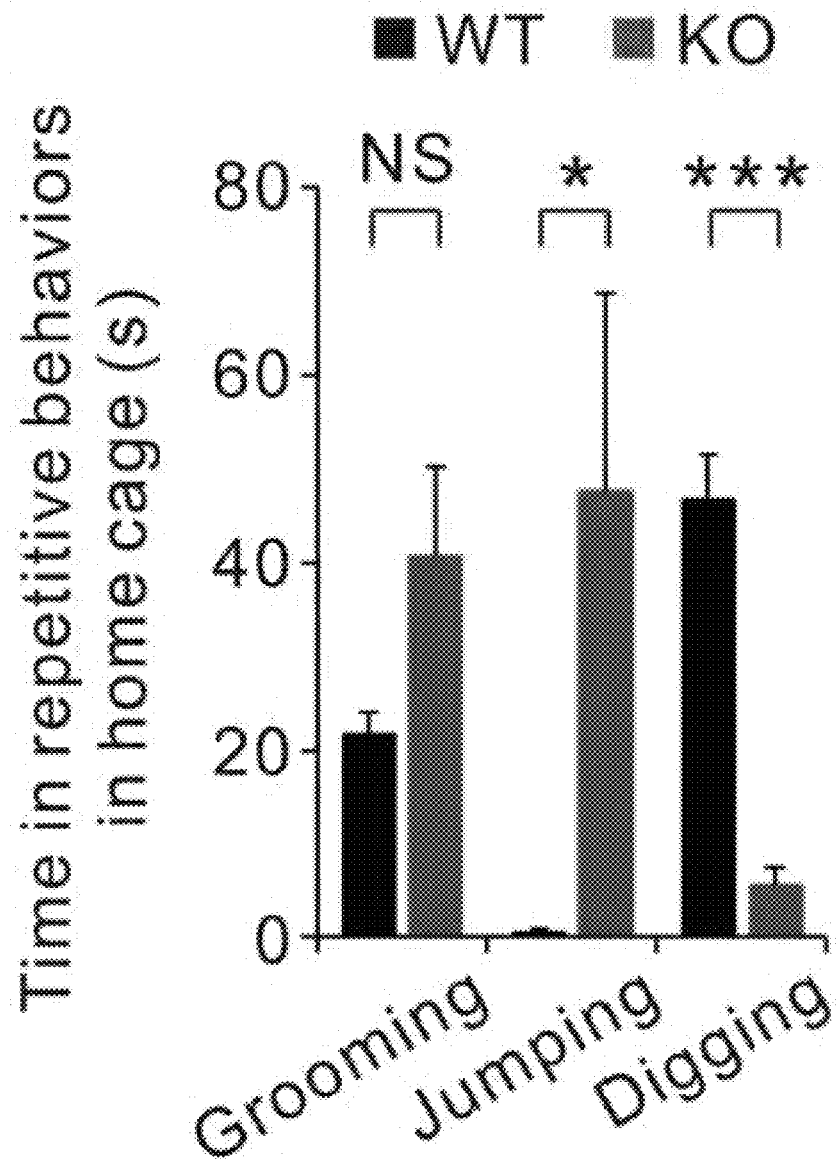

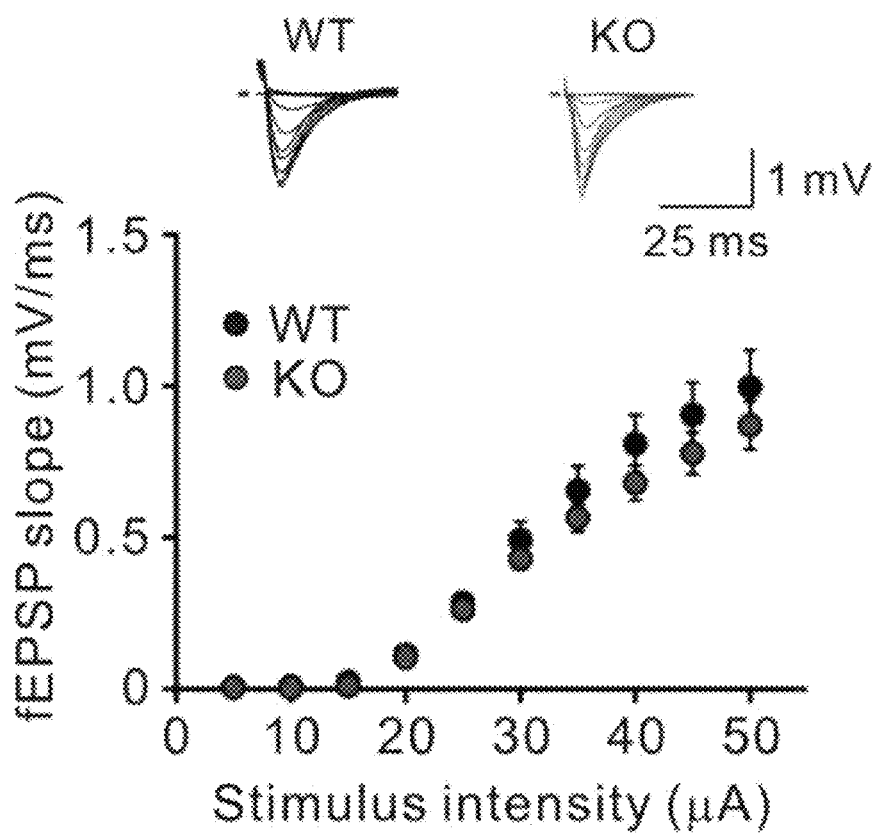

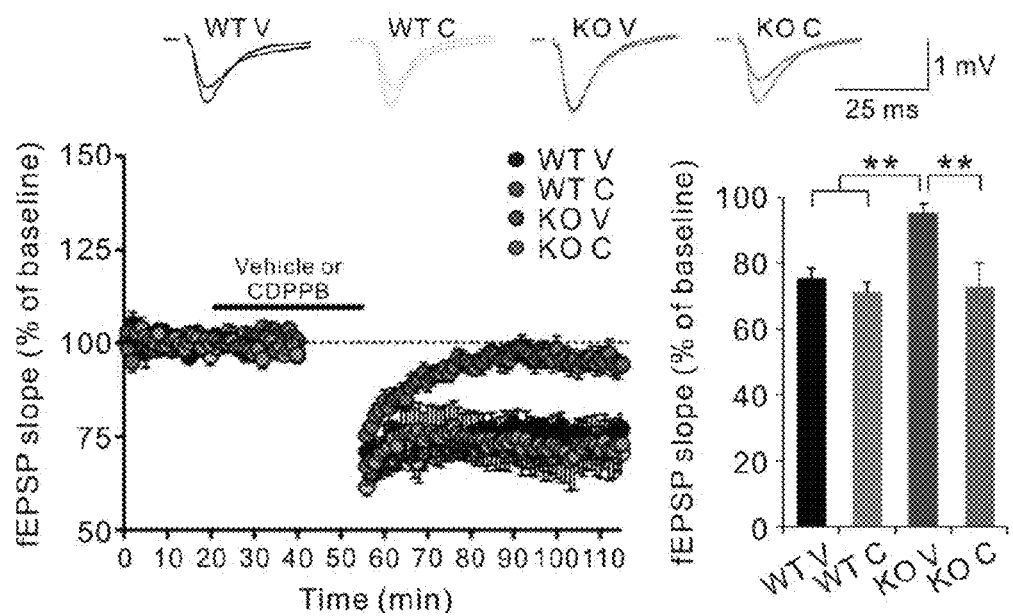

GENETICALLY ENGINEERED MOUSE MODEL FOR AUTISM SPECTRUM DISORDER HAVING DELETION OF *SHANK2* GENE AND USE THEREOF

CROSS-REFERENCE TO RELATED APPLICATION

This application claims priority to Application Ser. No. 61/679,186 filed Aug. 3, 2012, and Application No. 61/681,110 filed Aug. 8, 2012, which applications are incorporated herein by reference.

TECHNICAL FIELD

The present disclosure relates to a genetically engineered mouse model for Autism spectrum disorder (ASD) having a deletion of Shank2 gene and reduced function of NMDA receptor.

BACKGROUND ART

Autism spectrum disorder (ASD) is a developmental disorder that impairs social interaction and communication, causes one afflicted to have unstable feelings and emotions, and impairs cognitive development in many cases. ASD is also called a pervasive developmental disorder, because it is not a term that designates a kind of developmental disorder, but a term that designates, in a broad sense, diseases sharing various characteristic symptoms. In recent years, the prevalence of ASD in each country has increased, and thus the social and economical costs associated with ASD have increased and the quality of life of the patient's family has decreased. For this reason, studies on the establishment of the cause of ASD and the development of agents for treating ASD have been increasingly required. With respect to the cause of ASD, various risk factors have been studied, and genetic tendency, viral infection, abnormal metabolism and other environmental factors including rearing methods, have typically been known as risk factors and causes. However, specific evidence of the cause of development of ASD is still insufficient.

In recent years, studies on the genetic factors of ASD in animal models have been actively conducted, and various genes believed to have a close relation with ASD have been found through genetic studies on ASD patients. Because ASD shows a high heritability compared to other mental disorders, such studies on the genetic factors of ASD are important to widen the understanding of the biological causes of ASD and develop effective therapeutic agents against ASD. Shank2 protein is a scaffolding protein enriched at excitatory neuronal synapses and is known to interact with other various proteins in neuronal dendrites and play an important role in synapse signaling. As it has been reported that mutations in the Shank2 gene were found in ASD patients, it has been believed that the Shank2 gene is highly likely to be associated with ASD.

Accordingly, the present inventors have made extensive efforts to clarify the cause of ASD, and as a result, have found that the clinical features of ASD appear in a genetically engineered mouse carrying a deletion of the Shank2 gene.

SUMMARY

It is an object of the present disclosure to provide a genetically engineered ASD model mouse characterized by a deletion of the Shank2 gene and a reduced function of the NMDA receptor.

To achieve the above object, the present disclosure provides a genetically engineered model for ASD carrying a deletion of the Shank2 gene and having reduced NMDA receptor function.

In another embodiment, the present disclosure provides a method for producing an ASD genetically engineered model, the method comprising the steps of: (a) preparing an ASD-inducing transformation vector carrying a deletion of the Shank2 gene; and (b) introducing the transformation vector into the embryo of a mouse, thereby producing a mouse having reduced NMDA receptor function.

In still another embodiment, the present disclosure provides a method for screening a candidate therapeutic agent for ASD, the method comprising the steps of: (a) administering a candidate compound or compound to the above ASD genetically engineered model; (b) measuring an ASD symptom in each of the genetically engineered model treated with the candidate compound or composition (candidate group) and a genetically engineered model not treated with the candidate compound or composition (control group); and (c) selecting the candidate compound or composition if the ASD symptom in the candidate group is reduced compared to that in the control group.

In the present disclosure, exons 6 and 7 of the Shank2 gene may be deleted.

In the present disclosure, the genetically engineered model may be a mouse, and the genetically engineered model may show any one symptom selected from the group consisting of reduced social interaction, impaired communication, a repetitive behavior, and hyperactivity, which are the clinical characteristics of ASD.

In the present disclosure, the candidate compound or composition may be any one selected from the group consisting of natural compounds, synthetic compounds, RNA, DNA, polypeptides, enzymes, proteins, ligands, antibodies, antigens, bacterial or fungal metabolites, and bioactive molecules.

In still another embodiment, the present disclosure provides a pharmaceutical composition for treating ASD, comprising an agonist of NMDA receptor, and a pharmaceutical composition for treating ASD, comprising a positive allosteric modulator of metabotropic glutamate receptor 5 (mGluR5).

In the present disclosure, the agonist of NMDA receptor may be selected from the group consisting of D-alanine, D-serine, D-cycloserine, memantine, ketamine, aminoadamantane, neramexane, rimantadine and amantadine, and the positive allosteric modulator of metabotropic glutamate receptor 5 (mGluR5) may be CDPPB.

In addition to D-cycloserine used in the present disclosure, the NMDA receptor agonist may also show a therapeutic effect on ASD. For example, the NMDAR glycine-site partial agonist GLYX-13 showed a therapeutic effect on autism (Moskal et al. Neurosci Biobehav Rev 35, 1982-8 (2011)), and D-cycloserine is in clinical phase III trials for use as an agent for treating autism (Spooren et al. Trends in Pharmacological Sciences 33, 669-84 (2012)).

In the present disclosure, CDPPB was used as the positive allosteric modulator of mGluR5, and the effect thereof was identified, but the present disclosure is not limited thereto. Examples of the positive allosteric modulator of mGluR5 that may be used in the present disclosure include DFB, CPPHA, ADX47273, MPPA, VU0092273, VU0360172, VU-29 and the like (Cleva and Olive, Molecules 16, 2097-106 (2011)).

The pharmaceutical composition according to the present disclosure comprises a pharmaceutically acceptable carrier. Examples of the pharmaceutically acceptable carrier that is contained in the pharmaceutical composition of the present disclosure include, but are not limited to, lactose, dextrose, sucrose, sorbitol, mannitol, xylitol, starch, acacia gum, calcium phosphate, alginate, gelatin, calcium silicate, microcrystalline cellulose, polyvinyl pyrrolidone, cellulose, water, syrup, methyl cellulose, methyl hydroxybenzoate, propyl hydroxylbenzoate, talc, magnesium stearate and mineral oil, which are commonly used in formulation. The pharmaceutical composition of the present disclosure may comprise, in addition to the above components, a lubricant, a wetting agent, a sweetening agent, a flavoring agent, an emulsifying agent, a suspending agent, a preservative and the like. Suitable pharmaceutically acceptable carriers and formulations are described in detail in Remington's Pharmaceutical Sciences (19$^{th}$ ed., 1995). The pharmaceutical composition of the present disclosure may be administered orally or parenterally. For parenteral administration, the composition may be administered intravenously, subcutaneously, intramuscularly, intraperitoneally, transdermally, transmucosally or intraocularly.

The suitable dose of the pharmaceutical composition of the present disclosure may vary depending on various factors, including the formulation method, the mode of administration, the patient's age, weight and sex, the severity of the disease, diet, the time of administration, the route of administration, the rate of excretion, and reaction sensitivity. The dose of the pharmaceutical composition of the present disclosure may be 0.001-100 mg/kg (weight)/day, 0.01-80 mg/kg (weight)/day or 0.1-60 mg/kg (weight)/day for adults. In addition, the composition of the present disclosure may be administered once a day or several times a day at regular intervals according to the physician's or pharmacist's determination.

BRIEF DESCRIPTION OF THE DRAWINGS

FIG. 1a to FIG. 1j show that Shank2$^{-/-}$ mice display ASD (autism spectrum disorder)-like impaired social interaction and social communication, and repetitive jumping.

FIG. 2a to FIG. 2e show impaired NMDAR-dependent synaptic plasticity in Shank2$^{-/-}$ mice.

FIG. 4a to FIG. 4f show that CDPPB normalizes NMDAR function and substantially improves social interaction in Shank2$^{-/-}$ mice.

DETAILED DESCRIPTION

Generation of Shank2$^{-/-}$ Mice

Figure 1A:
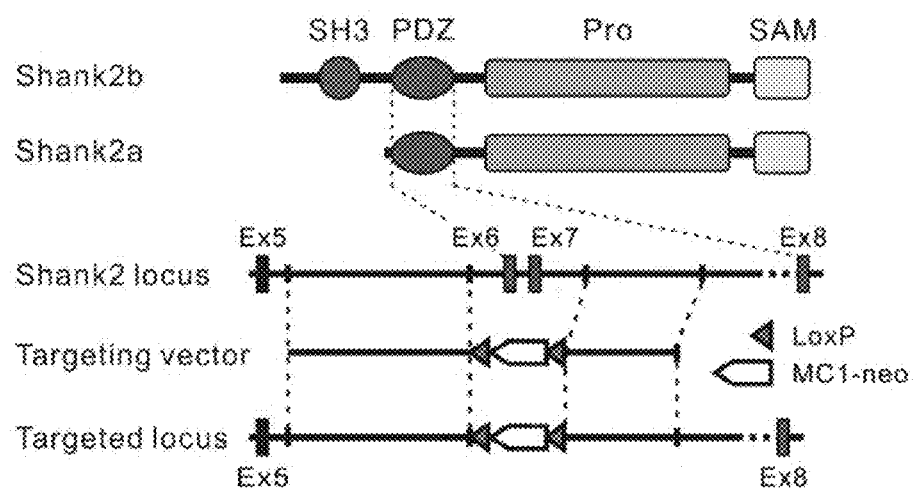

A targeting vector was designed to replace a ~3.1 kb genomic fragment of the Shank2 gene with a positive selection marker (MC1 promoter and neomycin resistance gene). In addition, a negative selection marker (HSV-1 promoter driven thymidine kinase gene) was appended to the construct to select against non-homologous recombination. To delete the exons 6 and 7 corresponding to the PDZ domain of Shank2 (exon numbers were assigned by cDNA sequence of Shank2b [NM_001113373]), 5'- and 3'-flanking DNA sequences were isolated from the 129/SvJ mouse genomic DNA by PCR using two sets of oligonucleotide primers. A 7.3 kb NotI-SalI fragment derived from a 5' region of Shank2 exon 6 was used as the left arm of the targeting vector: forward primer (NotI) 5'-AAG GAA AAA A GCGGCCGCACC CAG GAA CTG GGA ACC AGT AAC TGC TGA GAT CCT AGA GGC CAG TGG ATG GCC ATG TGT G-3'; reverse primer (SalI) 5'-TTC CGC GGC CGC TAT GGC CGA CGTCGACAT TTC AGT CCT ACC AGA GCC AAG GAG GGC AGC GGC TCC CT-3'. A 2.7 kb XhoI-NheI fragment derived from a 3' region of Shank2 exon 7 was used as the right arm: forward primer (XhoI) 5'-CCG CTCGAGAAA GCA GGA TAA TGT TGG TCA TTT GAG GAG TCT TCT TGT GTG CAA GTG TTG GTG TCT GTG AAC GTC ACC TGC GGG TTG TAT GTT GGT GCC AGT GAG GAA-3'; reverse primer (NheI) 5'-CTA GCTAGCCCT AAG CGA TTT AGT CTA ACA GCC ATG GAC AAA GCC TTT ACT ATA TAG TGT AAG CAT GGA GTG CTG CTC TCA AGT CTC AA-3'. The 5'-long arm and 3'-short arm fragments were subcloned into the pOsdupdel plasmid. The targeting vector was linearized with NotI and electroporated into 129/SvJ mouse J1 embryonic stem cells. Clones resistant to G418 and gancyclovir were selected, and homologous recombination was confirmed by Southern blotting. The Shank2 gene was modified in 6 of 210 clones screened.

The three clones containing the targeted mutation were injected into C57BL/6N blastocysts, and these were subsequently transferred into pseudopregnant foster mothers. The resulting male chimeric mice were bred to C57BL/6N females to obtain heterozygous Shank2 (Shank2$^{+/-}$) mice. Germ-line transmission of the mutant allele was verified by Southern blot analysis of tail DNA from F1 offspring with agouti coat color. Interbreeding of the heterozygous mice was performed to generate homozygous Shank2-deficient (Shank2$^{-/-}$) mice. After initial confirmation of the deletion of Shank2 gene in mice, Shank2$^{+/-}$ mice were established and maintained by backcrossing to C57BL/6 mice for more than five generations. The mice were bred and maintained according to the Yonsei Medical Center, KAIST and Seoul National University Animal Research Requirements, and all procedures were approved by the Committees on Animal Research at Yonsei Medical Center (protocol number 09-127), KAIST (KA2010-18) and Seoul National University (SNU-110809-1). Mice were fed ad libitum and housed under 12-h light cycle. For behavioral experiments, the present inventors used hetero×hetero breeding and strict sex-matched controls.

Characterization of Shank2$^{-/-}$ Mice

For Southern blot analysis, genomic DNAs obtained from J1 embryonic stem cells and mice were screened by a probe covering regions just outside the 3'-short arm of the knockout vector. The 947-bp Southern probe was generated by PCR using oligonucleotide primers (5'-CAC AGA GTG CCA GGA ATT CTG-3' and 5'-TGG AGG GAG CAG TAG TAT TGG-3'). Wild-type and mutant alleles of mice were confirmed by two sets of genotyping oligonucleotide primers; wild-type, 5'-GCT AGC ATG ACG TGT GTT GTG-3', 5'-CCG ACT GCA TCT GCG TGT TC-3' (PCR product size: 525 bp); Shank2$^{-/-}$, 5'-CCA CTG CAT CTG CGT GTT C-3', 5'-CCG ACT GCA TCT GCG TGT TC-3' (PCR product size: 591 bp).

RNA Extraction, cDNA Synthesis, RT-PCR, and Quantitative Real-time PCR

Total RNA was extracted from the pancreas and brain tissues of wild-type and Shank2$^{-/-}$ mice. Purified RNA samples were reverse transcribed by using the iScript™ Select cDNA Synthesis Kit (Bio-Rad, Hercules, Calif.) according to the manufacturer's instructions. The primers used in the RT-PCR analysis were primer 1 (Exon 6 Sense: GAC AAG ACG GTG GTC CTG), primer 2 (Exon 7 Sense TGC AGT ACC TGG AGT CCG), and primer 3 (Exon 12 Anti-Sense: GGA CCG TGG GCG TCA TTA). Exon numbers are based on Shank2b (NM_001113373). Reverse transcription for 60 min at 42° C. was followed by 30 PCR cycles. The PCR products were visualized by staining with ethidium bromide in a 2% agarose gel. Quantitative real-time PCR was performed by using the TaqMan Gene Expression Assay Kit (Applied Biosystems) according to the manufacturer's instructions. Briefly, 1 mL of cDNA was mixed with 10 mL of 2× TaqMan Universal Master Mix and 1 mL of the 20× TaqMan Gene Expression Assay, and was brought to a total volume of 20 mL with RNase-free water. Target amplification was performed in 96-well plates by using StepOnePlus™ Real-Time PCR System (Applied Biosystems). TaqMan probes for Shank2 (Mm01163746_mH and Mm01163737_m1) and glyceraldhyde-3-phosphate dehydrogenase (Gapdh) (Mm99999915_g1) were purchased from Applied Biosystems. Mm01163746_mH probe recognizes exons 3-4, whereas Mm01163737_m1 recognizes exons 15-16. PCR thermal cycling conditions included an initial 10 minutes at 95° C. to activate the AmpliTaq Gold DNA polymerase, followed by 40 cycles of denaturation (15 seconds at 95° C.) and annealing/primer extension (15 seconds at 60° C.). All samples were performed in triplicate. The relative RNA expression levels were calculated via a comparative threshold cycle ($C_t$) method using Gapdh as control: $\Delta Ct=Ct$ (Gapdh)–$C_t$(Shank2). The gene expression fold change, normalized to the Gapdh and relative to the control sample, was calculated as $2^{-\Delta\Delta Ct}$.

Social Interaction Assay in Home Cages

Stranger mice (2-4 months old) were placed in a transparent plastic apparatus (15×8×12 cm). In the beginning, the empty apparatus without a stranger mouse was placed in the home cage of a test mouse (wild-type or Shank2$^{-/-}$ mouse). After 10 minutes of free exploration of the container by the test mouse, a stranger mouse was placed in the apparatus, and the test mouse was allowed to explore the stranger mouse for 10 min. Exploration was defined as each instance in which wild-type or Shank2$^{-/-}$ mouse tries to sniff the stranger mouse, or orients its nose towards and come close to the stranger. Experiments and analyses were performed by independent researchers in a blind manner.

Three-chamber Social Interaction Assay

The three-chamber social interaction assay consisted of three phases. In the first phase, a wild-type or Shank2$^{-/-}$ mouse was placed in the three-chambered apparatus with two small containers in the left or right (not center) chamber, and was allowed to explore the environment freely for 10 min for habituation. After 10 min, the wild-type or Shank2$^{-/-}$ mouse was gently guided to the center chamber, and the two entrances to the center chamber were blocked while an inanimate object (Object) and a stranger mouse (Stranger 1) were placed in the two containers. Then, the two entrances were opened to allow the mouse in the center to explore the new environment freely for 10 min. In the third phase, the test mouse was gently guided to the center chamber again, with the blockade of the entrances. The Object was replaced with Stranger 2, followed by exploration of the Stranger 1 or 2 by the test mouse for 10 min. Exploration was defined as each instance in which wild-type or Shank2$^{-/-}$ mouse tries to sniff Object/Stranger, or orients its nose towards and come close to Object/Stranger. Time spent in each chamber was measured by Ethovision 3.1 program (Noldus). Individual movement tracks were analyzed by Ethovision and modified by ImageJ to generate heat maps. In addition to time spent in chamber or in exploration, the present inventors used the preference index, which represents a difference in percent exploration time over the targets (Wang, X. et al. Hum Mol Genet 20, 3093-108 (2011)).

Olfactory Function Test

This experiment was performed as described previously (Yang, M. & Crawley, J. N., Curr Protoc Neurosci Chapter 8, Unit 8 24 (2009)). A piece of a Kimwipes tissue was soaked with 20 µl of water or non-social cues (banana and coffee). To generate social cues, several Kimwipes tissues were introduced to a stranger mouse's cage for 2 days before the experiment. The wipers were retrieved from the stranger mouse's cage right before the experiment, and used for social cues. These non-social and social cues were contained in small round shaped Petri dishes with holes. Wild type (WT) or Shank2$^{-/-}$ mice were introduced for 30 min before the experiment. Water, non-social cues, and social cues were introduced sequentially to the homecages of WT or Shank2$^{-/-}$ mice for 6 min each. Cues were retrieved from the homecage after each session, and inter-session interval was 1 min. The sniffing behavior toward cue-containing petri dishes was measured in a blind manner.

Morris Water Maze Assay

Mice were trained to find a hidden platform (10 cm diameter) in a 120 cm diameter white plastic tank. Mice were given 3 trials per day with an inter-trial interval of 1 hr. Training was performed for six consecutive days, and the probe test was given for 1 min with the platform removed from the pool at day 7 (24 h after the last training session). Percentage of time spent in four quadrants of the pool (T, target; O, opposite; L, left; R, right), the number of exact crossings over the platform area, and swimming speed were evaluated by Ethovision 3.1 program (Noldus).

Novel Object Recognition Assay

Object recognition test was performed in an open field apparatus. During the sample phase, mice were allowed to explore two identical objects for 10 min. Test phase, where one of the two objects was replaced with a new one, was performed 24 h later, and exploration time for the two objects was measured. Object exploration was defined as each instance in which a mouse's nose touched the object or was oriented toward the object and came within 2 cm of it.

Ultrasonic Vocalization (USV)

To induce courtship USVs in male mice, a female was introduced into the male resident cage. USV recordings were made with 12-week-old male mice. Each male was isolated in a transparent acrylic housing cage for at least three days before the recording of their courtship USVs. On the recording day, mice were placed in the recording chamber for 30 min. After a 5 min background recording, one randomly chosen estrus B6 female (3-5 months old, 4-5 mice housed together) was placed in the recording chamber. The estrus stage was confirmed in female mice. A male was allowed to investigate the female for 5 min, and emitted USVs were recorded. USVs were recorded through a quarter-inch microphone and amplified with a preamplifier and a main amplifier (sound recording from Brüel and Kjaer Inc., Denmark). Signals were filtered from 1 Hz to 100 kHz and digitized with a sampling frequency of 250 kHz, 16 bits per sample, using a 1000 Hz high-pass digital filter (model 1322A, Axon Instruments, Union City, Calif.). Sound recordings were processed using a custom Matlab program. Short-time Fourier transform analysis was performed to draw sonograms (1,024 samples/block, ¼ overlap, resulting in a time resolution of 1.02 ms and a frequency resolution of 0.45 kHz). Frequencies lower than 35 kHz were filtered out to reduce background white noise and audible squeaking from females. As a basal power spectrum, consecutive powers of 10 s without USVs were sampled and averaged for time, such that 1.2 times the basal power spectrum was subtracted from each power spectrum and frequencies with a power less than zero were set to zero. This procedure was used to reduce the background white noise.

Pup Retrieval Assay

Virgin female mice were isolated for four days before pup retrieval assays. Three normal pups (1-d old; C57BL/6N) were placed at three different corners of a home cage of a test female mouse (wild-type or Shank2$^{-/-}$), and the female mouse was allowed to retrieve the pups for 10 min. Efficiency of pup retrieval was measured by the time taken to retrieve the first, second, and third pups.

Repetitive Behaviors

Mice in their home cages with fresh bedding were used to measure times spent in repetitive behaviors including jumping, upright scrabbling, grooming, and digging during 10 min. Jumping was defined as the behavior of a mouse where it rears on it hind legs at the corner of the cage, or along the side walls, and jumps so that the two hind legs are simultaneously off the ground. Upright scrabbling was defined as the behavior of a mouse where it rears on it hind legs at the corner of the cage, or along the side walls, and tries to climb up against the wall with the two hind legs alternatively or coordinately touching the ground. Grooming behavior was defined as stroking or scratching of face, head, or body with the two forelimbs, or licking body parts. Digging behavior was defined as the behavior of a mouse where it coordinately uses two fore legs or hind legs to dig out or displace bedding materials. Because Shank2$^{-/-}$ mice showed jumping behaviors significantly mixed with upright scrabbling behaviors, the present inventors could not separate the two behaviors, and labeled this behavior as jumping with the explanation in the text and figure legend.

Nest Building Assay

The isolated test mice were given a folded Kimwipes tissue as a nest-building material a day before the measurements of nesting behavior. The status of nesting material was photographed each day for 3 days. Nesting was scored based on the extent of conversion of the nesting material into fine pieces.

Open Field Assay

The size of the open field box was 40×40×40 cm, and the center zone line was 10 cm apart from the edge. Mice were placed in the center of chamber in the beginning of assay, and mouse movements were recorded with a video camera for 60 min, and analyzed by Ethovision 3.1 program (Noldus).

Elevated Plus-maze

The elevated plus-maze consisted of two open arms, two closed arms, and a center area, elevated to a height of 50 cm above the floor. Mice were placed in the center area and allowed to explore the space for 8 min.

Light-dark Test

The apparatus for light-dark test consisted of light (~600 lx) and dark (~5 lx) chambers adhered to each other. An entrance enabled mice to freely move across the light and dark chambers. The size of light chamber was 20×30×20 cm, and that of dark chamber was 20×13×20 cm. Mice were introduced to the center of the light chamber with their heads pointing towards the opposite side of the dark chamber, and allowed to explore the apparatus freely for 10 min. The latency to enter the dark chamber, the time spent in dark and light chambers, and the number of transitions were measured. Transition was defined as the translocation of all four feet of a mouse from one to another chamber.

Antibodies

GIT1 (Du139) (Premont et al., Proc Natl Acad Sci 95, 14082-7 (1998)) and PLC-β3 (Hwang et al., J Biol Chem 275, 16632-7 (2000)) antibodies were kind gifts from Drs. Premont and Suh, respectively. Antibodies against PSD-95 (#1402), Homer (#1133), and CaMKII (#1298) were generated in our laboratory. The following antibodies have been described: Shank2 (#1136) (Han, W. et al. *J Biol Chem* 281, 1461-9 (2006)), βpix (#1254) (Park, E. et al. *J Biol Chem* 278, 19220-9 (2003)), GKAP (#1243) (Ko, J. et al. *J Biol Chem* 278, 42377-85 (2003)), SynGAP (#1682) (Kim, M. H. et al. *J Neurosci* 29, 1586-95 (2009)), GluA1/GluR1 (#1193) (Kim, M. H. et al. *J Neurosci* 29, 1586-95 (2009)), GluA2/GluR2 (#1195) (Ko, J. et al. *J Biol Chem* 278, 42377-85 (2003)), and SAP97 (#1443) (Han, S. et al. *J Neurosci* 30, 15102-12 (2010)). The following antibodies were purchased: GIT1 and Shank2 N-term (NeuroMab); αPIX, phospho-PAK1/3 (Thr 423), ERK1/2, phospho-ERK1/2 (Thr 202, Tyr 204), mTOR, phospho-mTOR (Ser 2448), p38, and phospho-p38 (Thr 180, Tyr 182) (Cell Signaling); PAK1, PAK3, (Santa Cruz); GluN1/NR1, vGlut1, vGAT (SySy); glutamate, α-tubulin, □-actin (Sigma); GluN2A/NR2A (Invitrogen); GluN2B/NR2B (BD Transduction Laboratories); phospho-CaMKII□ (Thr 286), GABA (Abcam); NeuN, GAD67, phospho-GluR1 (Ser 831), phospho-GluR1 (Ser 845), phospho-GluN2B (Ser 1303), mGluR1, mGluR5 (Millipore).

Preparation of Whole Brain Homogenates and Synaptosomes

For whole brain homogenates, mouse brains (3-4 wks) were briefly homogenized in 3 volumes of ice-cold homogenization buffer (0.32 M sucrose, 10 mM HEPES pH7.4, 2 mM EDTA, protease inhibitors, phosphatase inhibitors). Protein concentrations were measured by the Bradford assay. The relative amount of □α-tubulin was used as a loading control. Synaptosomal fractions were prepared (Blackstone, C. D. et al., J Neurochem 58, 1118-26 (1992)).

Immunohistochemistry

Brains were isolated from adult mice (3 months old) after cardiac perfusion (4% paraformaldehyde). After the post-fixation for 12 h, 50 μm brain sections were obtained by vibratome. Brain sections were washed 3 times with phosphate-buffered saline for 10 min, permeabilized with 0.5% TritonX-100 for 30 min, blocked with 5% bovine serum albumin (BSA) for 1 h, stained with primary antibodies at 4° C. for 12 h, stained with secondary antibodies for 1 h, and mounted with Vectashield (Vector). For quantitative analysis, images of brain sections were captured with a confocal microscope (×5 and ×63 objectives; Leica Microsystems) and analyzed using Metamorph (Molecular Devices).

Pharmacological Rescue

CDPPB (Ascent scientific) was dissolved in DMSO and polyethylene glycol 400 (DMSO:PEG 400=1:9) to a final concentration of 6 g/l. Wild-type and Shank2$^{-/-}$ mice received intraperitoneal injection of CDPPB (10 or 3 mg/kg), or the same volume of DSMO-PEG400 mixture, 30 min before three-chamber or other behavioral assays and 40 min before brain sample preparation for immunoblot analyses. D-cycloserine (Ascent Scientific) was dissolved in saline to final concentration of 12 g/l. Wild-type and Shank2$^{-/-}$ mice received intraperitoneal injection of D-cycloserine (20 mg/kg), or the same volume of saline, 30 min before three-chamber assays.

Hereinafter, the present disclosure will be described in detail with reference to examples. It is to be understood, however, that these examples are for illustrative purposes only and are not intended to limit the scope of the present disclosure.

EXAMPLE 1

Construction of Shank2$^{-/-}$ Mice

Figure 1B:
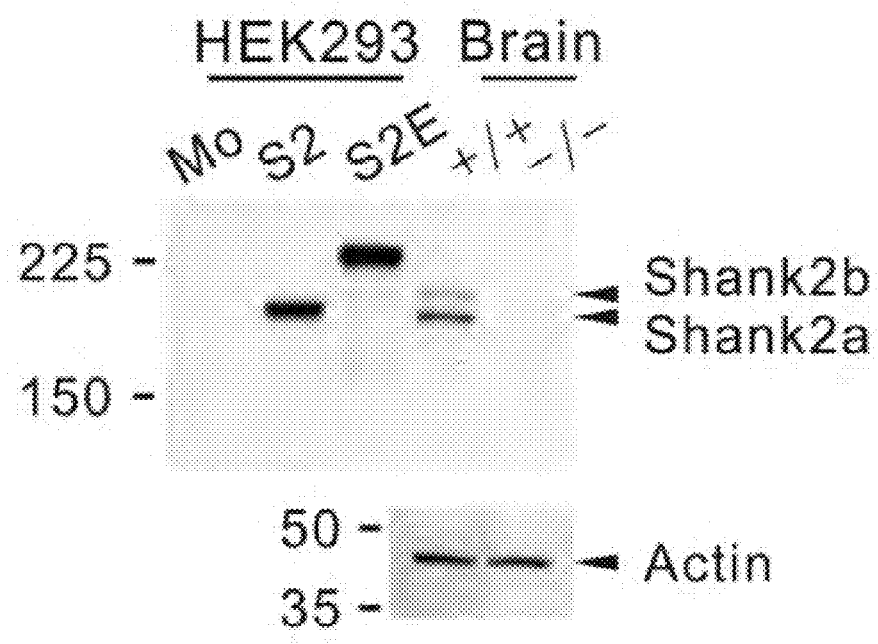

SHANK2 microdeletion that was found in some ASD patients leads to a loss of exons 6 and 7 and a frame shift, with concomitant removal of the PDZ and following domains in Shank2 proteins. To explore the possibility that this deletion of the Shank2$^{-/-}$ gene causes autism spectrum disorder (ASD) in humans, and to study the mechanisms underlying the development of ASD, the present inventors generated genetically engineered mice carrying a mutation identical to the human microdeletion (exons 6+7 deletion and a frame shift). This mutation affects both splice variants of Shank2 (Shank2a and Shank2b) in mice (FIG. 1a). The deletion of the Shank2$^{-/-}$ gene was verified by Southern blotting and various PCR methods. Shank2 proteins were undetectable in the brain (FIG. 1b), and there were no compensatory increases in Shank1 or Shank3. The Shank2$^{-/-}$ mice showed normal reproduction and brain structure.

EXAMPLE 2

Examination of Social Interaction Ability of Shank2$^{-/-}$ Mice

Figure 1C:
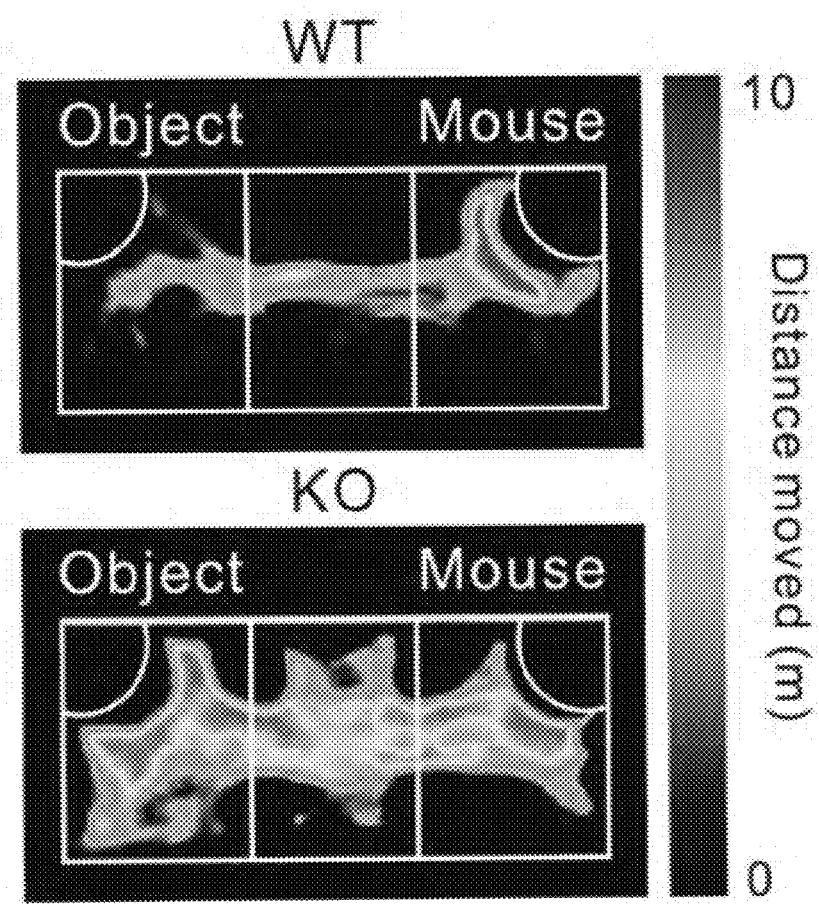
Figure 1D:
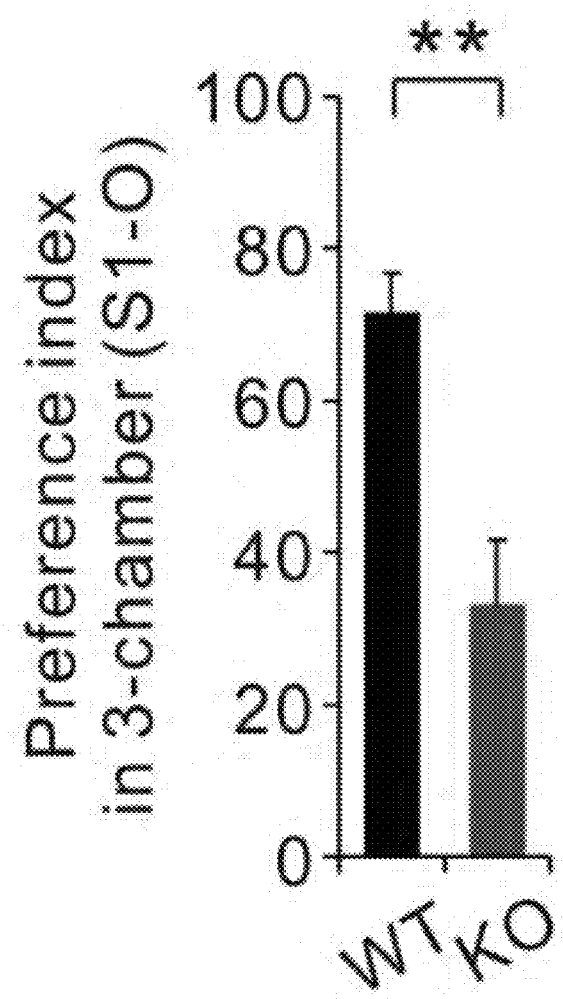
Figure 1E:
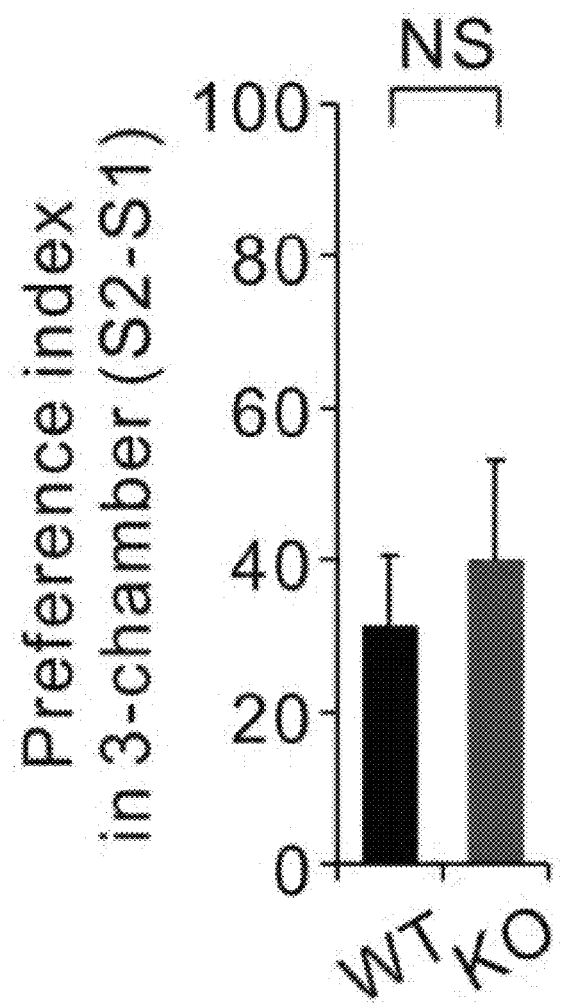

The present inventors examined whether Shank2$^{-/-}$ mice displayed autistic-like impairments in social interaction. In a home-cage social interaction assay, Shank2$^{-/-}$ mice showed reduced interaction with normal target mice, as compared with wild-type animals. In a three-chamber social interaction assay, wild-type animals preferred to explore Stranger 1 rather than Shank2$^{-/-}$ mice (FIGS. 1c and 1d). Next, when the object was replaced by a novel mouse (Stranger 2), Shank2$^{-/-}$ mice preferred to explore Stranger 2 over Stranger 1, similar to the action of wild-type animals (FIG. 1e), indicative of normal levels of social novelty recognition. Similar results were obtained when the present inventors used juvenile Shank2$^{-/-}$ mice. Shank2$^{-/-}$ mice had normal olfactory function.

Shank2$^{-/-}$ mice showed impaired spatial learning and memory in the Morris water maze, although novel object recognition memory was normal. These results suggest that Shank2$^{-/-}$ mice have partially impaired learning and memory, consistent with exons 6+7 deletion in humans which causes autism spectrum disorder (ASD) and mild to moderate mental retardation.

Figure 1F:
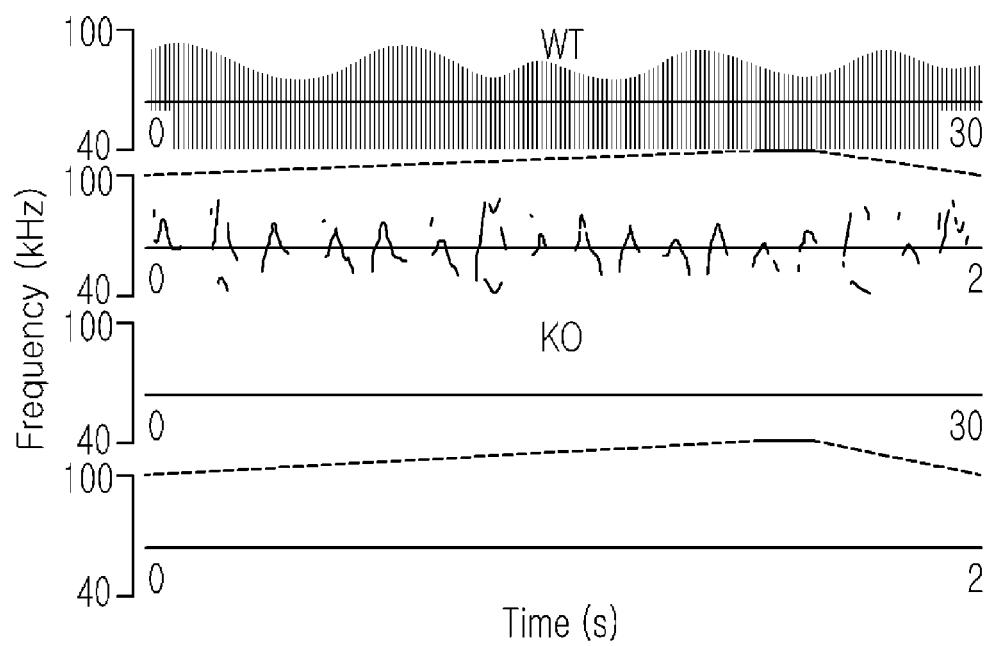
Figure 1G:
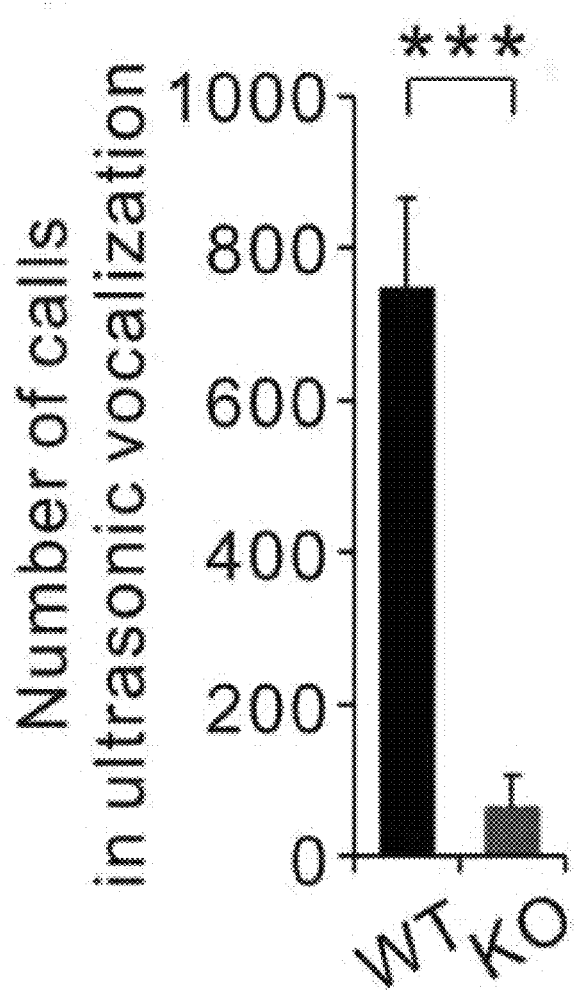
Figure 1H:
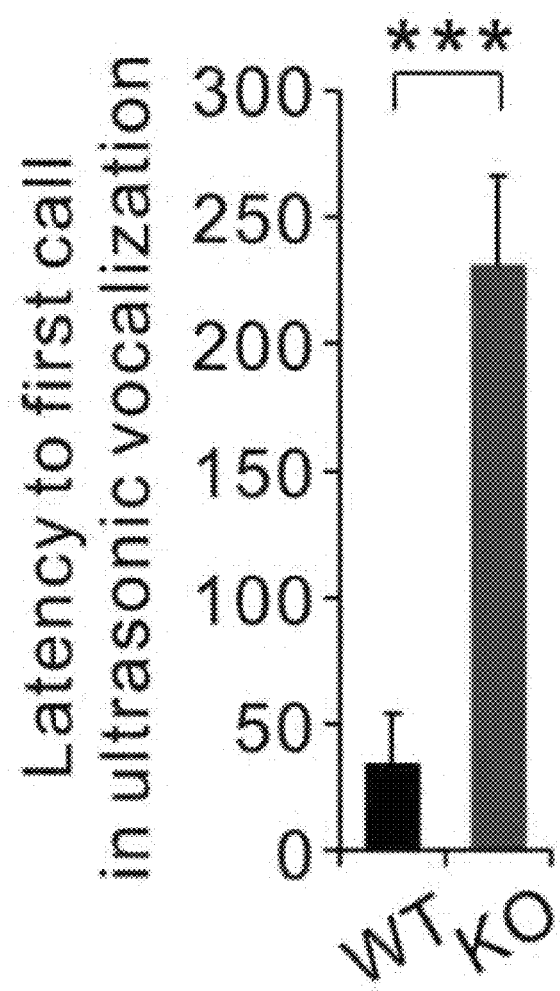

Shank2$^{-/-}$ mice displayed impairments in social communication by ultrasonic vocalizations (USVs). When allowed to interact with a novel wild-type female mouse, Shank2$^{-/-}$ male mice uttered USVs less frequently than did wild-type animals, and took longer to make the first call (FIGS. 1f to 1h). In a pup retrieval assay, Shank2$^{-/-}$ female mice retrieved the pups less efficiently than wild-type mice.

Shank2$^{-/-}$ male animals displayed other autistic-like abnormalities. When kept alone in stranger-free home cages, Shank2$^{-/-}$ mice showed enhanced jumping mostly mixed with upright scrabbling, normal grooming, and decreased digging behaviors (FIG. 1j). Shank2$^{-/-}$ mice also displayed impaired nesting behavior, hyperactivity in assays including the open field test, anxiety-like behavior in an elevated plus-maze, and increased grooming in a novel object recognition arena. Shank2$^{-/-}$ female mice showed similar repetitive jumping, hyperactivity in an open field, and anxiety-like behavior in an elevated plus-maze, although not in a light-dark box. These data collectively suggest that Shank2$^{-/-}$ mice display ASD-like behaviors. It should be noted that the hyperactivity and anxiety-like behaviors might contribute to the impaired social interaction in Shank2$^{-/-}$ mice by limiting target exploration or evoking anxiety-like responses.

The present inventors also characterized heterozygous Shank2 (Shank2$^{+/-}$) mice because human gene mutations are mostly heterozygotic. Shank2$^{+/-}$ mice showed hyperactivity, similar to Shank2$^{-/-}$ mice. However, Shank2$^{+/-}$ mice showed no abnormalities in social interaction, repetitive behaviors, or anxiety-like behaviors, reflecting intrinsic differences between humans and mice.

EXAMPLE 3

Examination of Reduced NMDAR Function in Shank2$^{-/-}$ Mice

Shank2/ProSAP1 is an important regulator of excitatory synaptic structure and function (Sheng et al. *J Cell Sci* 113, 1851-6 (2000); Ehlers, M. D. *Curr Biol* 9, R848-50 (1999); Hayashi, M. K. et al. *Cell* 137, 159-71 (2009)). Shank2 deletion, however, had minimal effects on excitatory or inhibitory synapses. In addition, electron microscopy revealed that excitatory synapse number and postsynaptic density morphology were unaltered.

Figure 2B:
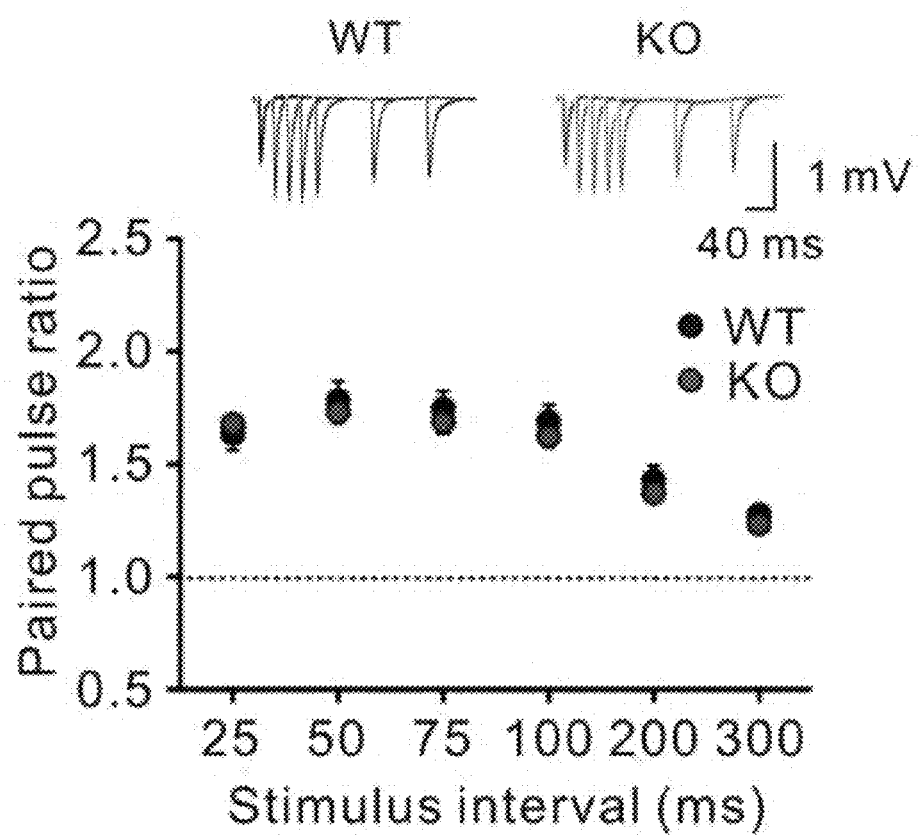
Figure 2C:
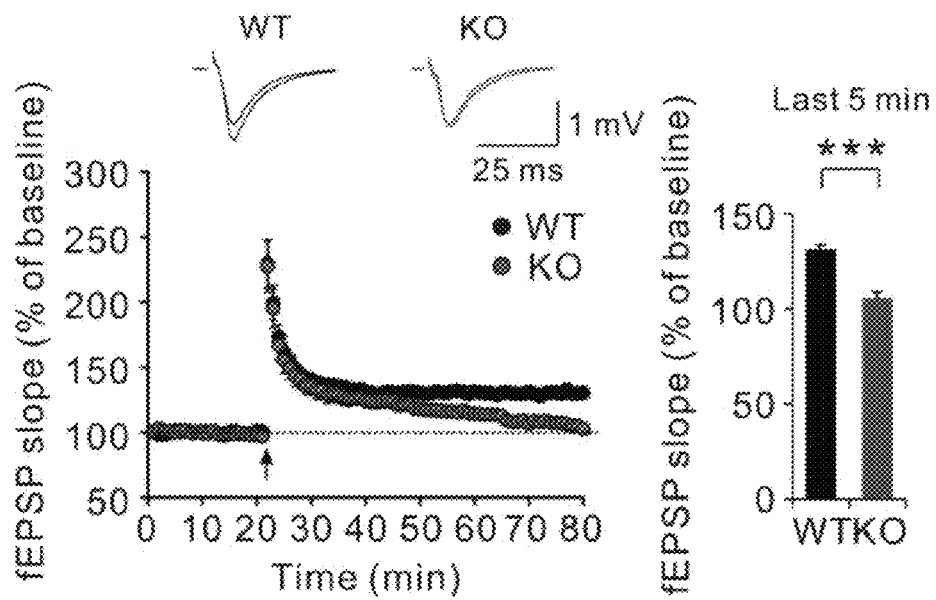
Figure 2D:
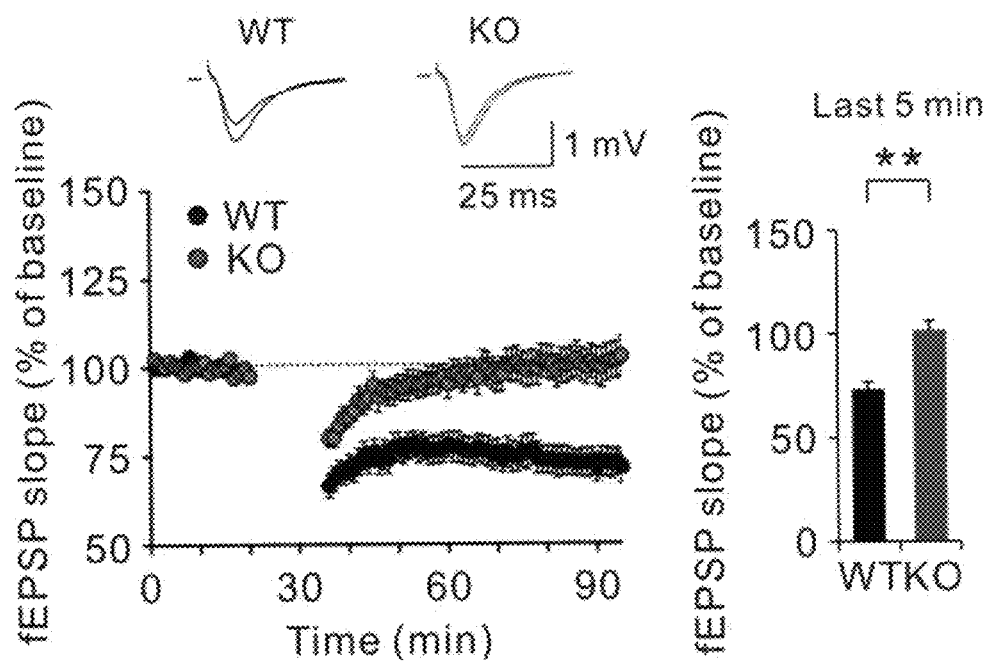

Next, the present inventors measured synaptic transmission at hippocampal Schaffer collaterals-CA1 pyramidal (SC-CA1) synapses. Basal excitatory transmission such as input-output and paired-pulse ratio was unchanged in Shank2$^{-/-}$ mice (FIGS. 2a and 2b). In addition, spontaneous transmission and membrane excitability were normal in mutant animals. When synaptic plasticity was tested, long-term potentiation (LTP) induced by high frequency stimulation or theta-burst stimulation were severely impaired in Shank2$^{-/-}$ mice (FIG. 2c). Long-term depression (LTD) induced by low-frequency stimulation was completely abolished also in Shank2$^{-/-}$ mice (FIG. 2d). Because LTD induced by low-frequency stimulation activates both NMDA and metabotropic glutamate receptors (NMDARs and mGluRs), the present inventors isolated mGluR-LTD by bath-applying DHPG, an agonist of mGluR5, but found no difference between genotypes. This suggests that the observed reductions in LTP and LTD may be due to NMDAR hypofunction.

Figure 2E:
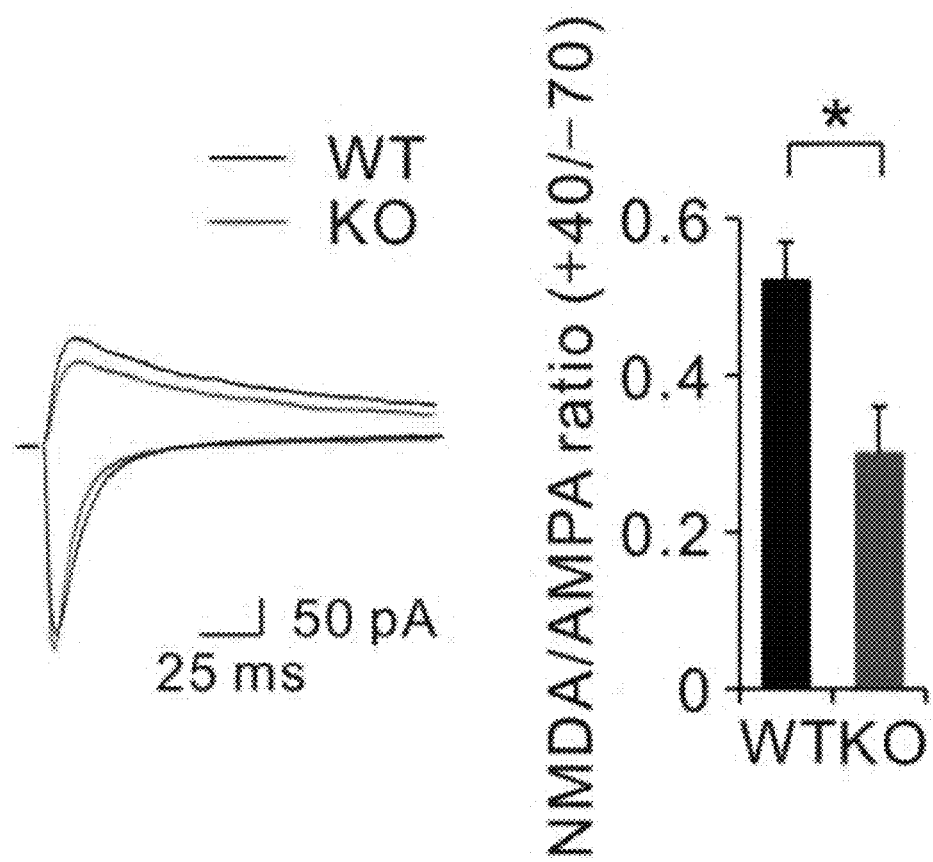

Thus, the present inventors measured the NMDA/AMPA ratio at Shank2$^{-/-}$ SC-CA1 synapses. Indeed, the NMDA/AMPA ratio was reduced relative to wild-type synapses (FIG. 2e). Meanwhile, both the decay kinetics of NMDAR-EPSCs and NR2B-mediated EPSCs were indistinguishable between genotypes, suggesting that NR2A- and NR2B-containing NMDARs were equally affected. Given that AMPAR-mediated transmission isnormal (FIG. 2a), these results suggest that NMDAR-mediated transmission is selectively decreased. The NMDA/AMPA ratio in the medial prefrontal cortex, however, was unaltered in Shank2$^{-/-}$ mice, suggesting that the reduced NMDA/AMPA ratio is not a change uniformly occurring in all brain regions.

Shank2 deletion may also affect NMDAR-associated signaling that it critically regulates various synaptic events including LTP and LTD (Zhu, J. J. et al. *Cell* 110, 443-55 (2002); Shepherd, J. D. & Huganir, R. L. *Annu Rev Cell Dev Biol* 23, 613-43 (2007)). In immunoblot analyses, phosphorylation but not total levels of CaMKIIα/β (T286), ERK1/2 (p42/44), and p38 were significantly reduced in the Shank2$^{-/-}$ brain. A similar decrease was observed in phosphorylation of the AMPAR subunit GluA1 (S831 and S845). There were no changes in phosphorylation of PAK1/3 and mTOR, total levels of glutamate receptors (GluN2A, GluA2, and mGluR1/5), or total levels of synaptic scaffolds and signaling adaptors/proteins directly or indirectly associated with Shank2 including PSD-95, SAP97, GKAP, SynGAP, Homer, α/βPIX, GIT1, and PLC-β3. The increase in GluN1 expression may reflect a compensatory increase. These results suggest that Shank2 deficiency leads to impairments in NMDAR-associated signaling.

EXAMPLE 4

Experiment on Restoration of NMDAR Function Shank2$^{-/-}$ Mice

Figure 3A:
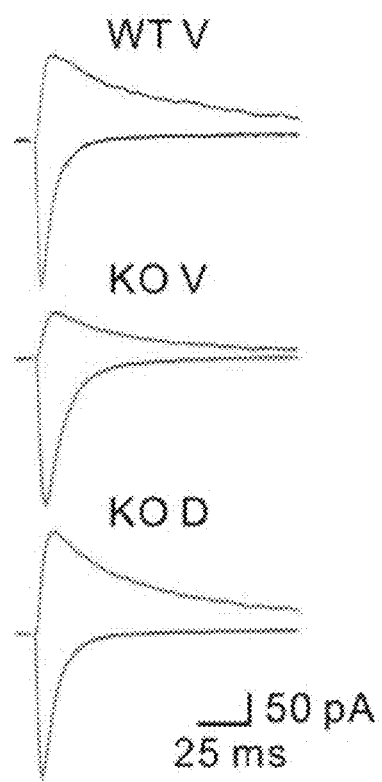
FIG. 3a to FIG. 3d show that D-cycloserine normalizes NMDAR function and improves social interaction in Shank2$^{-/-}$ mice.
Figure 3A:
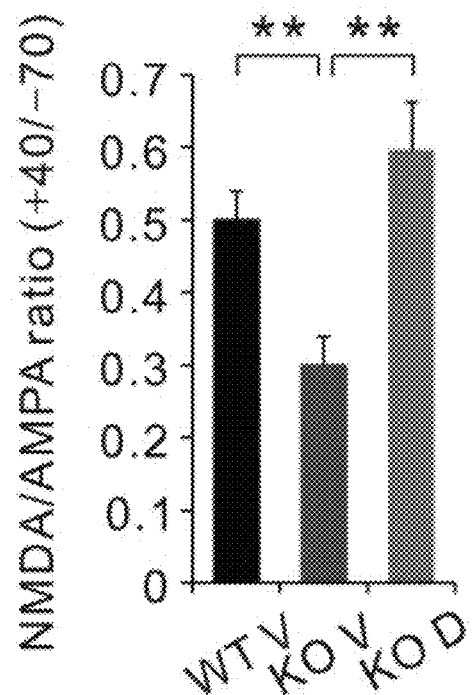
Figure 3B:
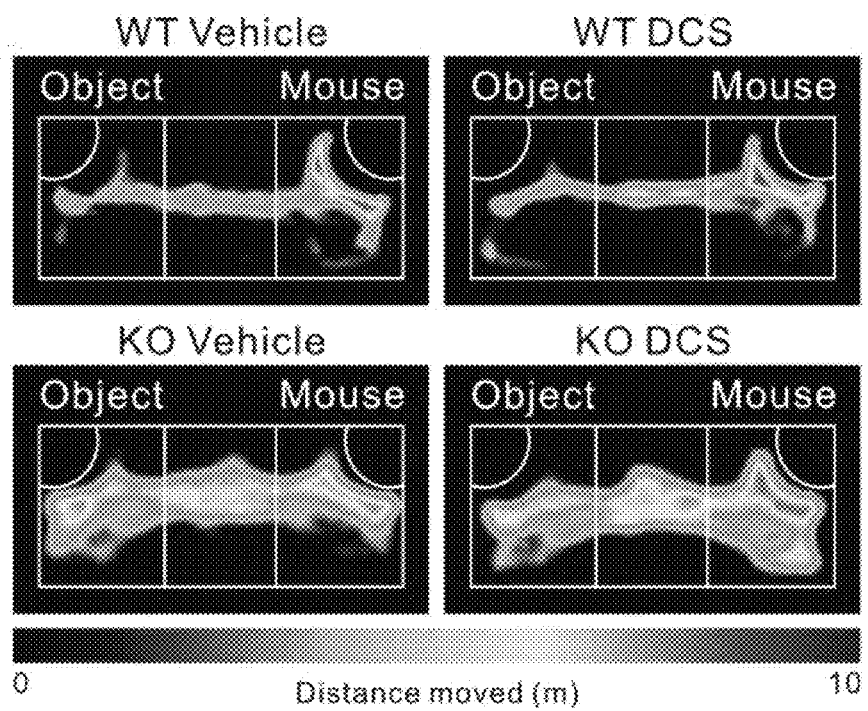
Figure 3C:
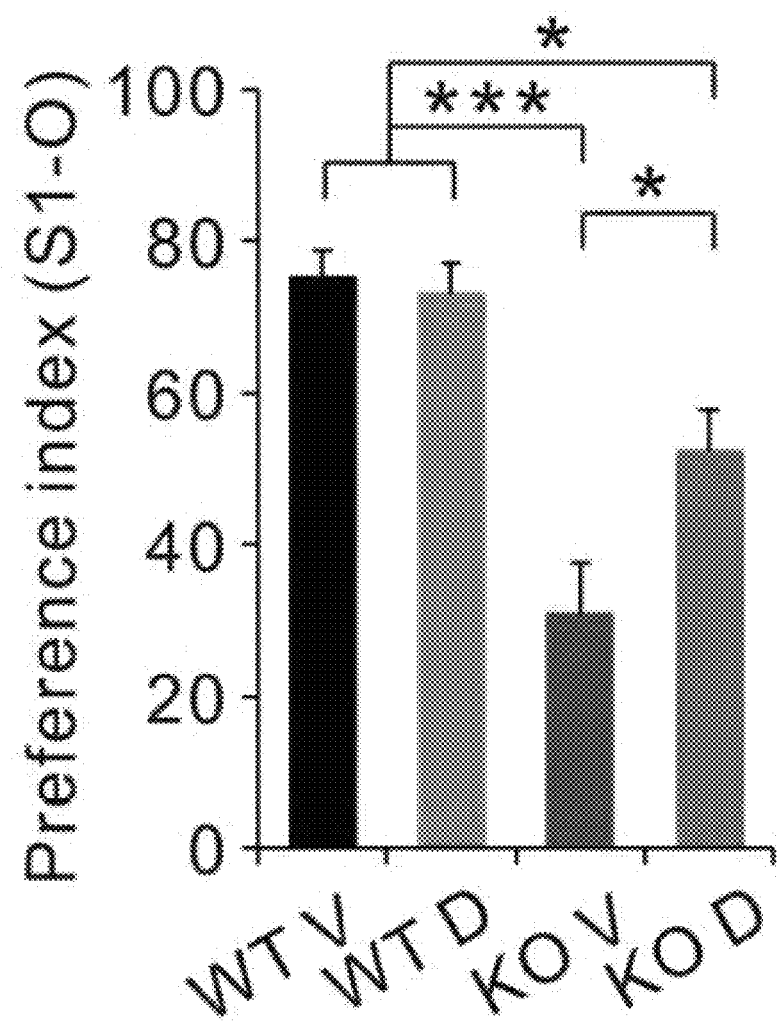
Figure 3D:
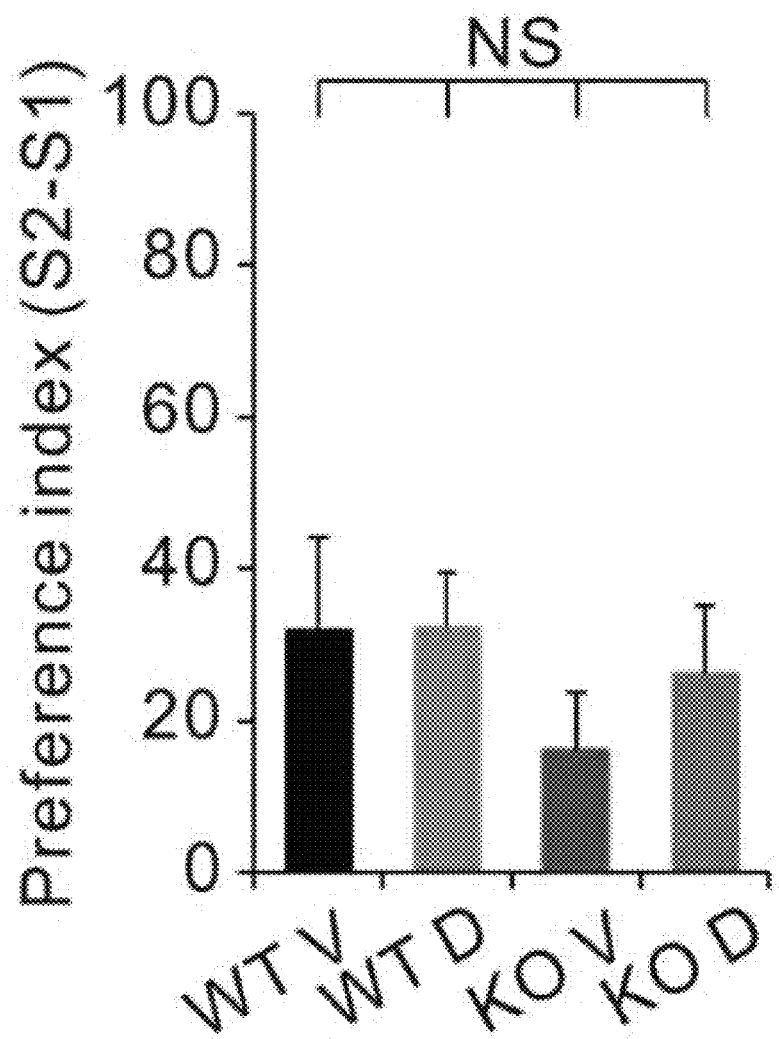

Reduced NMDAR function and associated signaling may contribute to autism spectrum disorder (ASD)-like behaviors in Shank2$^{-/-}$ mice. To directly test this hypothesis and restore NMDAR function, the present inventors used D-cycloserine, a partial agonist at the glycine-binding site of NMDARs, which has been shown to rescue repetitive grooming in neuroligin-1-deficient mice associated with a reduced NMDA/AMPA ratio (Blundell, J. et al. *J Neurosci* 30, 2115-29 (2010)). As a result, the present inventors found that D-cycloserine fully recovered the NMDA/AMPA ratio (FIG. 3a). In addition, D-cycloserine-treated Shank2$^{-/-}$ mice showed improved social interaction in three-chamber social interaction assays (FIGS. 3b to 3d).

To further explore the association between reduced NMDAR function and ASD-like behaviors in Shank2$^{-/-}$ mice, the present inventors used CDPPB, a membrane-permeable positive allosteric modulator of mGluR5, which increases the responsiveness of mGluR5 to glutamate and enhances NMDAR function (Gregory, K. J. et al. *Neuropharmacology* 60, 66-81 (2011); Uslaner, J. M. et al. *Neuropharmacology* 57, 531-8 (2009); Verpelli, C. et al. *J Biol Chem* 286, 34839-50 (2011)). CDPPB has anti-psychotic and pro-cognitive activities and facilitates behavioral flexibility. In addition, CDPPB restores reduced excitatory transmission and ERK phosphorylation caused by Shank3 knockdown (Verpelli, C. et al. *J Biol Chem* 286, 34839-50 (2011)), and CDPPB and its derivative (VU-29) enhance both LTP and LTD, and spatial learning (Ayala, J. E. et al. *Neuropsychopharmacology* 34, 2057-71 (2009)).

Figure 4A:
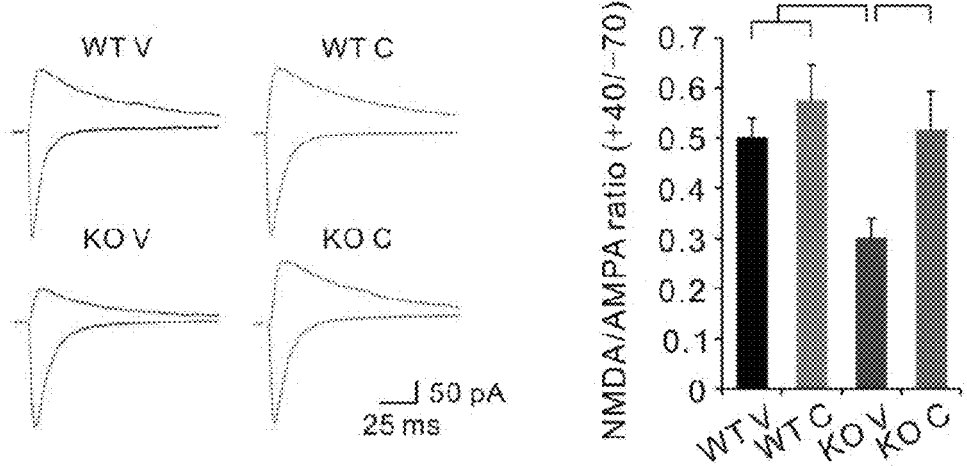
Figure 4B:
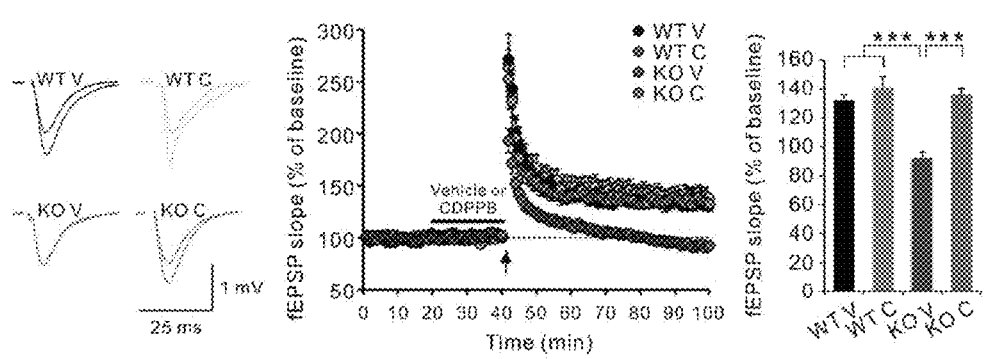
Figure 4D:
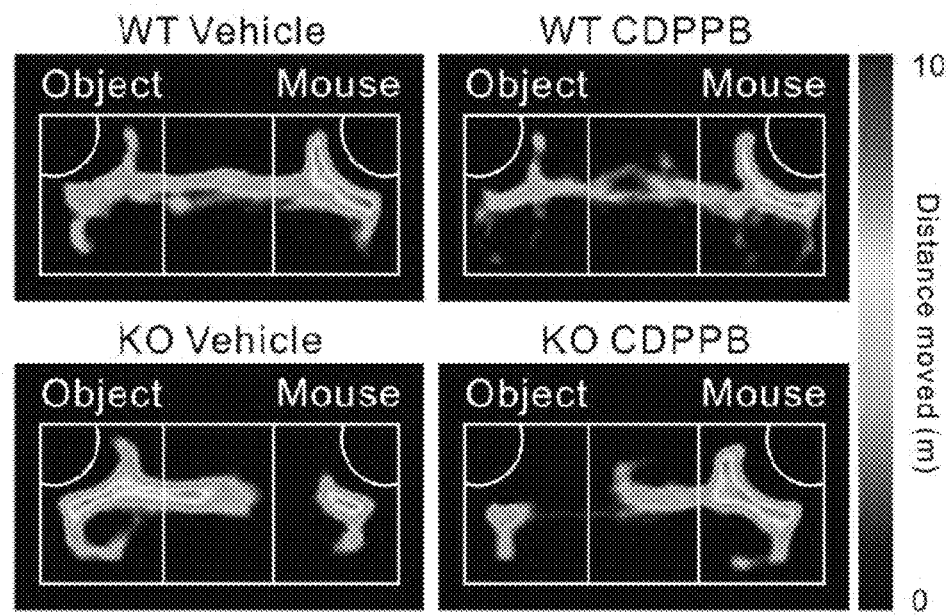
Figure 4E:
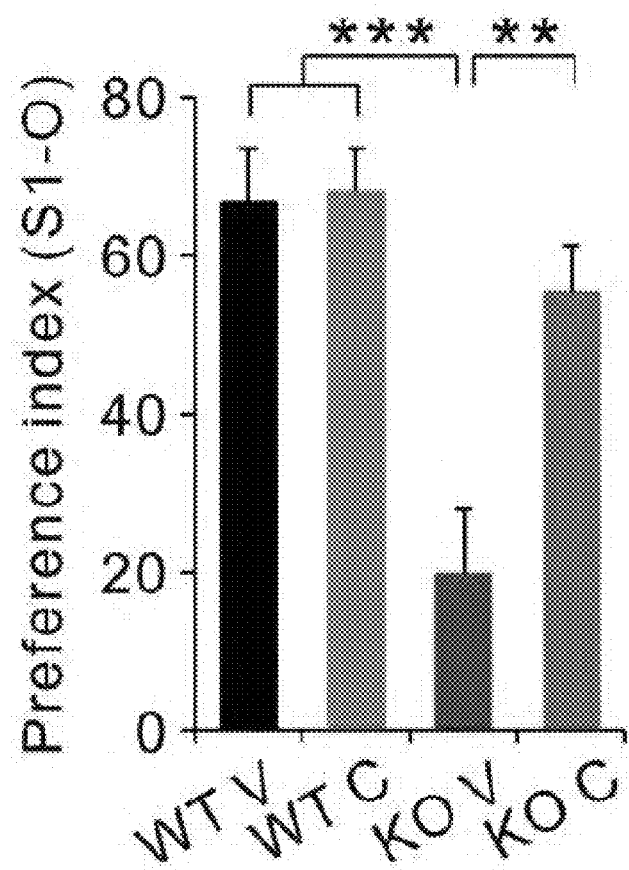
Figure 4F:
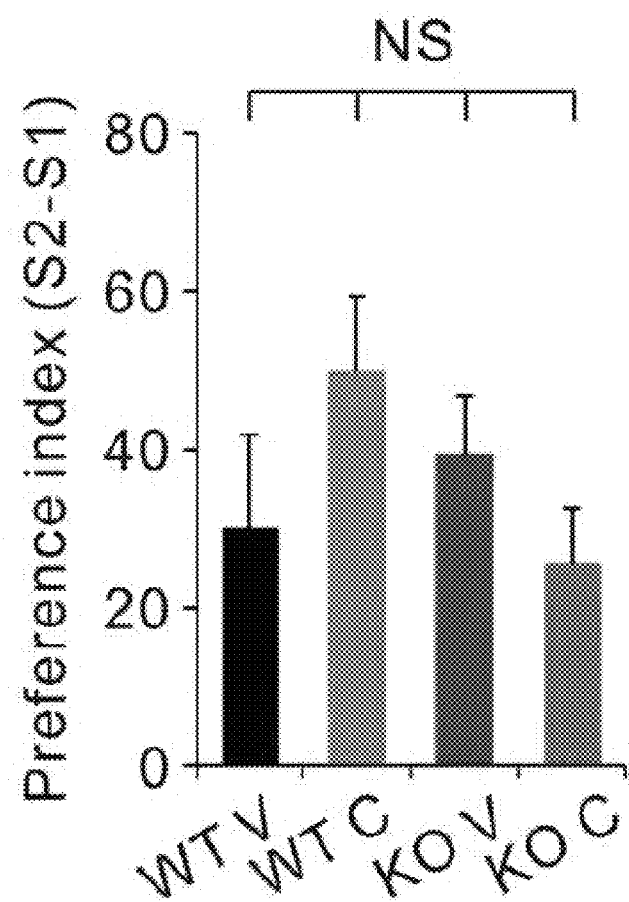

Consistent with previous findings, CDPPB also normalized the NMDA/AMPA ratio in Shank2$^{-/-}$ slices (FIG. 4a). Moreover, CDPPB restored the impaired LTP and LTD at SC-CA1 synapses (FIGS. 4b and 4c), without affecting basal synaptic transmission. Biochemically, CDPPB treatment of Shank2$^{-/-}$ mice fully normalized NMDAR signaling in Shank2$^{-/-}$ whole brains and also in Shank2$^{-/-}$ synaptosomes. The smaller extents of signaling deficits in older mice (8 weeks) relative to younger mice (3-4 weeks) may reflect age-dependent reductions in NMDAR-mediated currents, and/or compensatory changes in NMDAR signaling.

Behaviorally, Shank2$^{-/-}$ mice treated with CDPPB exhibited substantial recoveries in social interaction to an extent greater than D-cycloserine, while having no effect on social novelty recognition. A lower-dose CDPPB did not rescue impaired social interaction, indicative of a dose-dependent action. Notably, CDPPB did not rescue impaired pup retrieval, repeated jumping, anxiety-like behaviors, and hyperactivity. These results, together with the D-cycloserine results, suggest that reduced NMDAR function and signaling lead to impaired social interaction in Shank2$^{-/-}$ mice.

As described above, according to the present disclosure, genetically engineered mice that show the clinical features of ASD due to the deletion of the Shank2 gene can be obtained, and the genetically engineered mice can be effectively used to screen candidate therapeutic agents.

Although the present disclosure has been described in detail with reference to the specific features, it will be apparent to those skilled in the art that this description is only of a preferred embodiment thereof, and does not limit the scope of the present disclosure. Thus, the substantial scope of the present disclosure will be defined by the appended claims and equivalents thereof.

What is claimed is:

1. A genetically engineered mouse model for Autism spectrum disorder (ASD) whose genome comprises a deletion of a Shank2 gene and reduced function of a N-methyl-D-aspartate (NMDA) receptor, wherein the deletion includes exons 6 and 7 from the Shank 2 gene, and the genetically engineered mouse model is homozygous for the deletion of the Shank2 gene and has any one or more symptoms selected from the group consisting of reduced social interaction, impaired communication, a repetitive behavior, and hyperactivity, which are clinical features of ASD.

* * * * *